United States Patent [19]

Riley

[11] Patent Number: 5,309,750
[45] Date of Patent: May 10, 1994

[54] POUCH TESTER

[76] Inventor: David C. Riley, 39 Holland Crescent, Kingston, Ont., Canada, K7M 2V7

[21] Appl. No.: 937,871

[22] PCT Filed: Apr. 5, 1991

[86] PCT No.: PCT/CA91/00115
§ 371 Date: Oct. 19, 1992
§ 102(e) Date: Oct. 19, 1992

[87] PCT Pub. No.: WO91/16611
PCT Pub. Date: Oct. 31, 1991

[30] Foreign Application Priority Data

Apr. 18, 1990 [CA] Canada .................. 2014813

[51] Int. Cl.⁵ .............................. G01M 3/36
[52] U.S. Cl. ........................... 73/52; 73/49.3
[58] Field of Search .......... 73/49.3, 52, 37, 40, 73/715, 716

[56] References Cited

U.S. PATENT DOCUMENTS

| | | | |
|---|---|---|---|
| 3,805,595 | 4/1974 | Dobry | 73/49.3 |
| 4,671,101 | 6/1987 | Franklin | 73/49.3 |
| 4,697,452 | 10/1987 | Prakken | 73/52 |

FOREIGN PATENT DOCUMENTS 0513931  11/1992  European Pat. Off. ............ 73/52

Primary Examiner—Hezron E. Williams
Assistant Examiner—Michael Brock
Attorney, Agent, or Firm—Konrad S. Kaeding

[57] ABSTRACT

A portable device for testing a pouch containing a flowable substance and manufactured from flexible film. The device includes two plates. One of the plates is moveable towards the other and one has a pressure sensor mounted flush with a surface which faces the pouch to be tested. The pouch is placed between the plates and they are moved together, pressing the pressure sensor against the pouch.

2 Claims, 1 Drawing Sheet

POUCH TESTER

BACKGROUND OF THE INVENTION

1. Field of the Invention

The present invention relates to an apparatus for testing the film or seal integrity of pouches which contain flowable materials.

2. Description of the Related Art

It is well known to package flowable materials, for example, milk, on so-called vertical form and fill machines. Using such a machine, a flat web of synthetic thermoplastic film is unwound from a roll and formed into a continuous tube in a tube forming section, by sealing the longitudinal edges of the film together to form a so-called lap seal or a so-called fin seal. The tube thus formed is pulled vertically downwards to a filling station. The tube is then collapsed across a transverse cross-section of the tube, the position of the cross-section being at a sealing device below the filling station. A transverse heat seal is made, by the sealing device, at the collapsed portion of the tube, thus making an airtight seal across the tube. The sealing device generally comprises a pair of jaws. After making the transverse seal, but before the jaws of the sealing device are opened, a quantity of material to be packaged, e.g. liquid, is caused to enter the tube, at the filling station, and fill the tube upwardly from the aforementioned transverse seal. The tube is then caused to move downwardly a predetermined distance. Such movement may be under the influence of the weight of the material in the tube, or may be caused by pulling or mechanically driving the tube. The jaws of the sealing device are closed again, thus collapsing the tube at a second transverse section. The second transverse section may be above, usually just above, the air/material interface in the tube, or the second transverse section may be below the air/material interface. The sealing device seals and severs the tube transversely at the second transverse section. The material-filled portion of the tube is now in the form of a pillow shaped pouch. Thus the sealing device has sealed the top of the filled pouch, sealed the bottom of the next-to-be formed pouch, all in one operation. One such vertical form and fill machine of the type described above is sold under the trade mark PREPAC. With some other machines, the sealing device does not sever the tube at the second transverse section, but does sever the tube subsequently. The portions of the pouch at the ends of the transverse seals are often referred to as "ears".

For many years, milk has been packaged in pouches made on vertical form and fill machines. Such pouches have been sold to household consumers and, in use, such milk-filled pouches are stood within an openmouthed pitcher. More recently, such pouches have been used to package other flowable comestibles, mayonnaise, salad dressings, preserves and the like. Pouches containing such comestibles are usually sold to "institutional" buyers, e.g. restaurants.

It is also known to package flowable materials in sachets which have seals around three or four sides of the sachet. Such sachets may contain portion-sized comestibles such as mustard, ketchup, sugar and the like. In the context of the present invention the term "sachet" is intended to come within the scope of the term "pouch".

Heretofore, the integrity of pouch seals has been tested by a number of methods. One entails dropping a number of pouches from a given height onto a hard floor. This method suffers from the disadvantage that after one drop of the pouch from a given height, the pouch may be weakened, and further drops from greater heights, until the pouch bursts or leaks, may not be truly indicative of the pouch's integrity. As used herein the term "integrity" means the ability of the pouch to remain whole, i.e. without leakage of material from inside the pouch. Another method involves squeezing and twisting the pouch by hand. Such a test is highly subjective and depends on the person doing the test. One commercially available pouch tester allows air pressure to be applied to the inside of the pouch via a needle inserted in the pouch. The air pressure is monitored by a pressure gauge connected to another needle inserted in the pouch. A major disadvantage of this tester is that the pouch integrity is destroyed by insertion of a needle into the pouch. Another commercially available tester places a pouch under vacuum inside a dome. This tester takes time to generate the high vacuum required and is therefore not very convenient. Another method of testing pouches which is more convenient and reliable is desired. Furthermore an apparatus which is portable would be very desirable.

SUMMARY OF THE INVENTION

Accordingly the present invention provides a portable apparatus for testing a pouch which contains a flowable material and is made from a flexible substantially gas impermeable thermoplastic polymeric film, said apparatus comprising two plates, at least one of which is moveable, one of said plates having a pressure sensing device located thereon such that the film of the pouch, when placed between the two plates and squeezed therebetween by said plates, presses against the pressure sensing device.

In one embodiment the two plates are hingedly connected.

BRIEF DESCRIPTION OF THE DRAWINGS

The present invention may be better understood by reference to the drawings.

DESCRIPTION OF THE PREFERRED EMBODIMENT(S)

Figure 1:
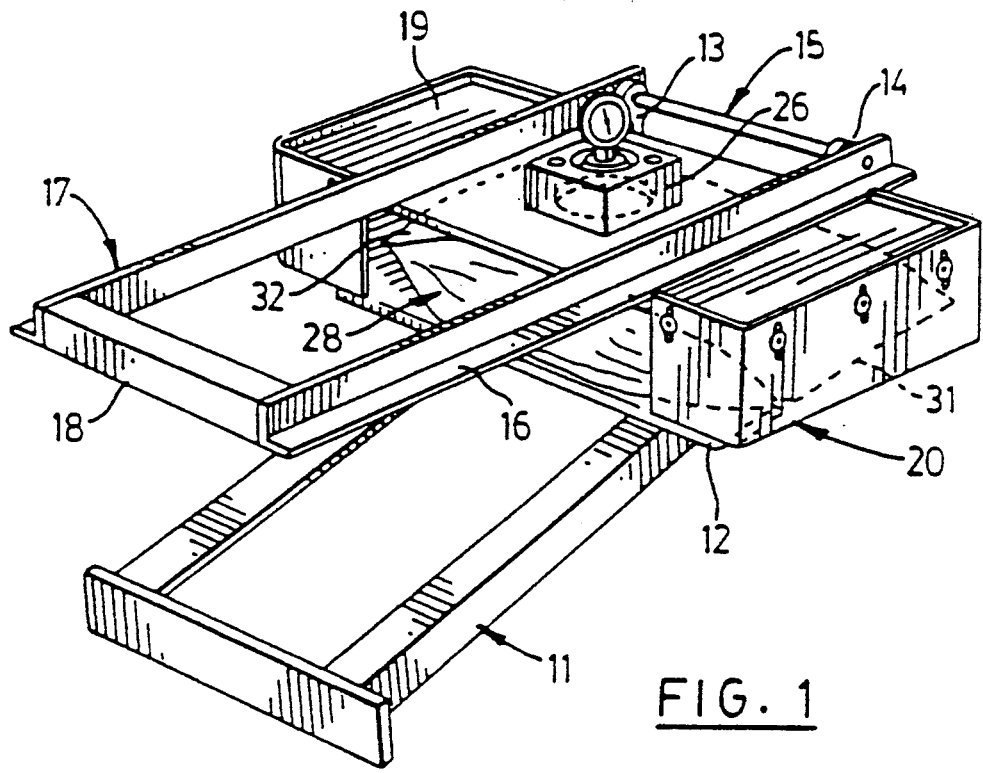
FIG. 1 shows one embodiment of a tester.
Figure 2:
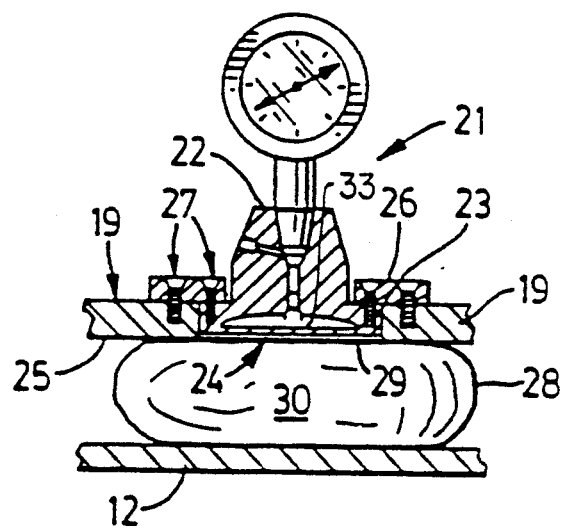
FIG. 2 shows the placing of the pressure sensing device in relationship to the pouch.

FIG. 1 shows base 11 upon which is attached stationary first plate 12. Extending perpendicularly from one edge of stationary plate 12 are two posts 13 and 14. Posts 13 and 14 have eyes at the end furthest from stationary plate 12. The height of posts 13 and 14 are adjustable by means (not shown). Inserted through the eyes is shaft 15. The ends of shaft 15 are connected to arms 16 and 17, and arms 16 and 17 are joined by handle 18. Arms 16 and 17 may be replaced by square tubes or similar, as will be understood by those skilled in the art. Attached to arms 16 and 17 is moveable plate 19. Posts 13 and 14 may have a plurality of staggered holes therein in lieu of eyes, to allow for adjustment of the distances of stationary plate 12 and moveable plate 19. Attached to the periphery of moveable plate 19 is a guard 20 which extends perpendicularly from moveable plate towards the periphery of stationary plate 12. Attached to moveable plate 19 is a pressure sensing assembly 21 which is shown in more detail in FIG. 2. Pressure assembly 21 comprises a pressure gauge 22 and a diaphragm unit 33 located in a hole 23 in moveable plate 19. Diaphragm unit 33 contains a diaphragm 24 which is bonded or welded to diaphragm unit 33. Diaphragm 24 is flush with the lower surface 25 of moveable plate 19. Pressure assembly 21 is held fast onto moveable plate 19 by split clamp collar 26 and screws 27. The apparatus is most conveniently made of metal, preferably aluminium.

In operation base 11 is placed on a hard surface such as a bench or the floor. Handle 18 is lifted so that moveable plate 19 is pivoted about shaft 15, thus raising moveable plate 19 away from stationary plate 12. A pouch 28 is placed on stationary plate 12 and handle 18 is depressed so that moveable plate 19 moves towards stationary plate 12. Guard 20 surrounds pouch 28. Diaphragm 24 contacts film 29 of pouch 28. As moveable plate 19 is moved towards stationary plate 12 pressure is applied to the material 30 inside pouch 28. This pressure is exerted on the film 29 and upon seals 31 and 32. If more and more pressure is exerted there will become a point where the seals start to leak, the film starts to leak or the pouch bursts. This is the point at which the pouch integrity is lost. The pressure at which the pouch integrity is lost is measured by the pressure reading appearing on gauge 22. As will be understood by those skilled in the art, pouches may be tested to a given pressure and provided the integrity of the pouch is still intact, the pouch "passes" the test. In general the tester is constructed such that the arms enable a mechanical advantage of 5:1 to be applied to the moveable plate. Application of about 445N to handle 18 generates 2 225N on the pouch. If the pouch is in contact with the stationary plate 12 over an area of about 25 cm by 12.5 cm then the pressure in the pouch would be about 69 kPa. If the tester is intended to be used on the floor it is advantageous to angle the gauge so that it is easier to read when the operator is standing. Additionally, the gauge preferably has a maximum pointer so that if the pouch bursts unexpectedly, the maximum reading is not lost. As will be understood by those skilled in the art, pressure transducers, piezoelectric sensors and the like may be used for the pressure sensing device.

I claim:

1. A portable apparatus for testing a pouch which contains a flowable material and is made from a flexible substantially gas impermeable thermoplastic polymeric film, said apparatus comprising two plates, at least one of which is moveable towards the other plate, a first plate of said plates having a pressure sensing device located thereon, said pressure sensing device having a diaphragm flush with a portion of said first plate which is intended to be in contact with said pouch, such that when the pouch is placed between the two plates and squeezed therebetween by said plates, the film of the pouch presses against the pressure sensing device.

2. An apparatus according to claim 1 wherein the two plates are hingedly connected.

* * * * *